United States Patent [19]

Kees, Jr. et al.

[11] 4,340,061
[45] Jul. 20, 1982

[54] ANEURYSM CLIP

[75] Inventors: George Kees, Jr., Alexandria, Ky.;
Set Shahbabian, Cincinnati, Ohio

[73] Assignee: Mayfield Education and Research Fund, Cincinnati, Ohio

[21] Appl. No.: 845,295

[22] Filed: Oct. 25, 1977

[51] Int. Cl.³ .............................................. A61B 17/12
[52] U.S. Cl. .................................... 128/325; 128/346; 24/261 C
[58] Field of Search ....................... 128/346, 325, 321; 24/261 C, 259

[56] References Cited

U.S. PATENT DOCUMENTS 3,604,425  9/1971  Le Roy .......................... 128/346 X
3,827,438  8/1974  Kees .................................. 128/346

*Primary Examiner*—Michael H. Thaler
*Attorney, Agent, or Firm*—James W. Pearce; Roy F. Schaeperklaus

[57] ABSTRACT

An aneurysm clip that includes a pair of elongated blades which are urged into gripping relation with an aneurysm on a blood vessel. The blades have smooth edges for positioning adjacent to the blood vessel when the blades grip the aneurysm. Teeth on edges of the blades spaced from the smooth edges thereof engage and grip the aneurysm spaced from the blood vessel.

2 Claims, 7 Drawing Figures

ANEURYSM CLIP

This invention relates to aneurysm occluding clips. More particularly, this invention relates to a spring operated aneurysm clip.

An aneurysm clip must hold firmly on an aneurysm without signficantly damaging fragile walls of a blood vessel from which the aneurysm protrudes. An object of this invention is to provide such a clip which includes elongated spring urged blades which engage walls of aneurysm adjacent the blood vessel and include intermeshing teeth which grip the aneurysm spaced from the blood vessel.

A further object of this invention is to provide such a clip in which the teeth are rounded and the teeth on each of the arms are turned toward the other arm so that the teeth intermesh.

It is important that an aneurysm clip not slip once it has been applied to an aneurysm notwithstanding continuous pulsation in an artery on which the aneurysm is formed. Concern as to the possibility of slippage has lead to production of stronger clips with high closure pressure on the blades as well as rough surfaces on opposed portions of the blades. A further object of this invention is to provide an aneurysm clip which firmly grips walls of an aneurysm without requiring excessive pressure on the blades or rough surfaces on blade faces and without rough or serrated edges adjacent the blood vessel on which the aneurysm is formed.

A further object of this invention is to provide an aneurysm clip having elongated blades each of which is provided with a smooth edge for placing adjacent a blood vessel and teeth along an opposed edge for intermeshing with similar teeth on the other blade and gripping a portion of the aneurysm protruding from the blood vessel.

Briefly, this invention provides a clip for positioning on a blood vessel which includes a pair of plate-like blades for engaging walls of an aneurysm on a blood vessel. A spring urges the arms into engagement with aneurysm walls with the arms in opposed substantially flatwise parallelism. Each of the blades carries a plurality of teeth along one edge thereof. The teeth on each blade are bent into overlapping relation with the other blade, and the teeth intermesh so that the teeth can firmly grip the aneurysm. Edges of the teeth are curved to avoid injury to fragile blood vessel walls. An opposed side of each blade is smooth for positioning adjacent the blood vessel with the teeth engaging the aneurysm spaced from the blood vessel.

The above and other objects and features of the invention will be apparent to those skilled in the art to which this invention pertains from the following detailed description and drawing, in which.

In the following detailed description and the drawing, like reference characters indicate like parts.

Figure 1:
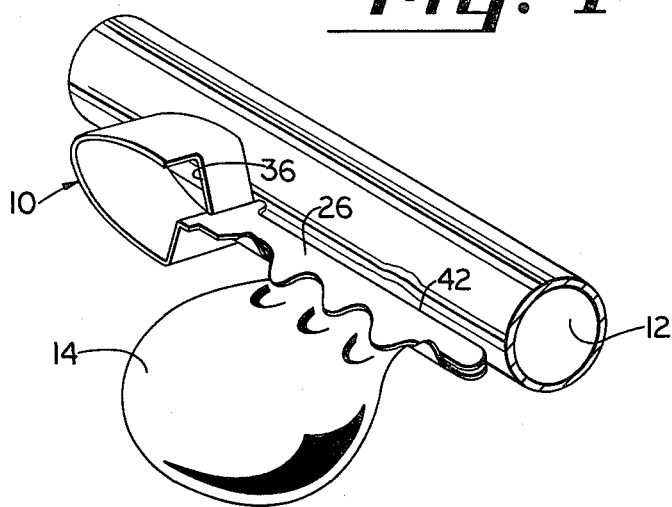
FIG. 1 is a perspective view of an aneurysm clip constructed in accordance with an embodiment of this invention, the clip being shown in association with a portion of a blood vessel having an aneurysm thereon.

In FIG. 1 is shown a clip 10 which is constructed in accordance with an embodiment of this invention. The clip 10 is shown in association with a blood vessel 12 on which an aneurysm 14 is formed.

Figure 3:
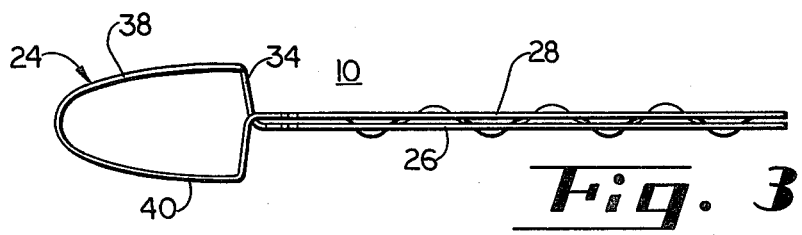
FIG. 3 is a view in side elevation of the clip shown in FIG. 1.
Figure 7:
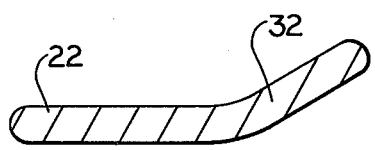
FIG. 7 is a view in section taken on the line 7—7 in FIG. 2.
Figure 2:
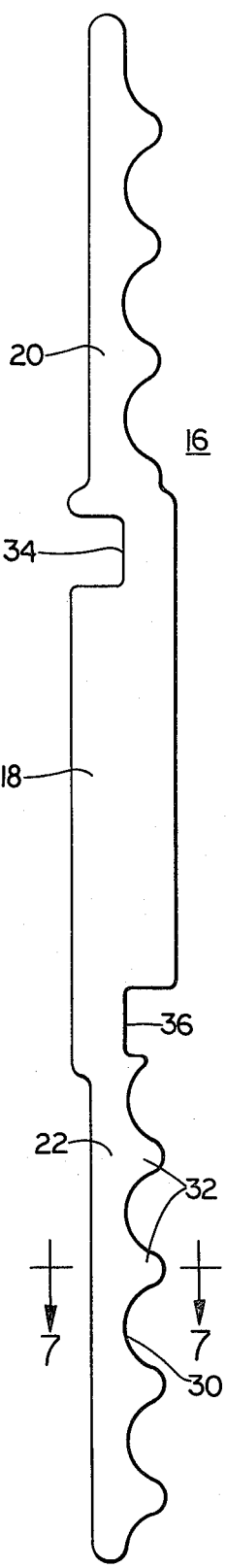
FIG. 2 is a plan view of a blank from which the clip of FIG. 1 is formed.

The clip 10 is formed from a blank 16 shown in FIG. 2. The blank 16 is formed of sheet spring metal and includes a central portion 18 and outwardly extending elongated arms 20 and 22. The central portion 18 forms a spring head 24 (FIGS. 3–5) of the clip 10, and the arms 20 and 22 form elongated blades 26 and 28 of the clip 10. Rounded scallops 30 (FIG. 2) are formed in one edge of each of the elongated arms 20 and 22 to define spaced teeth 32. Edges of the teeth 32 are rounded as shown. Main portions of the arms 20 and 22 can be flat. The teeth 32 are bent out of the plane of the main portions of the associated arms as shown in FIG. 7.

Figure 4:
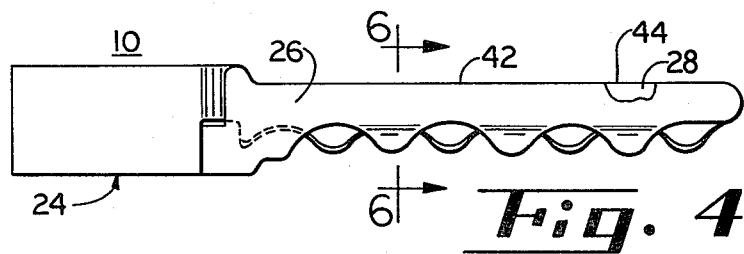
FIG. 4 is a plan view of the clip.
Figure 5:
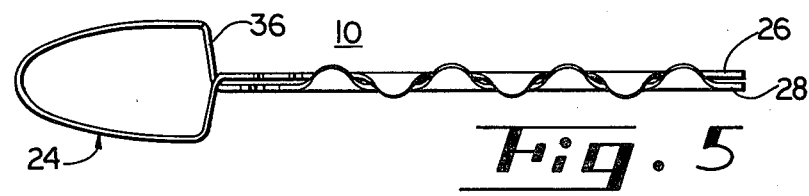
FIG. 5 is another view in side elevation of the clip.

Slots 34 and 36 are formed in opposed sides of the blank 16 between the central portion 18 and the arms 20 and 22, respectively. As shown in FIG. 4, when the central portion 18 is formed into the spring head 24, the slots 34 and 36 permit the blades 26 and 28 to separate when sides 38 and 40 of the spring head are advanced toward each other by means of an appropriate clip handling tool (not shown).

Edges 42 and 44 of the blades 26 and 28 opposed to the curved or scalloped edges are smooth and can be straight so that, when the clip 10 is mounted on the aneurysm 14, the smooth straight edges 42 and 44 are adjacent the blood vessel 12. The main portions of the blades 26 and 28 can be flat and smooth, and the spring of the spring head 24 urges the blades toward flatwise engaging relation with the walls of the aneurysm 14. The teeth 32 grip the aneurysm 14 along a line spaced from the blood vessel and engage a portion of the aneurysm which would otherwise be considered useless.

Figure 6:
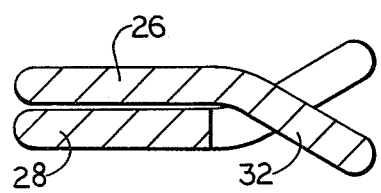
FIG. 6 is a view in section taken on the line 6—6 in FIG. 4.

As shown in FIG. 6, the teeth 32 on one blade can extend into alignment with the flat portion of the other blade, and the teeth intermesh so that the teeth 32 can firmly grip the aneurysm 14 spaced from the wall of the blood vessel.

Since the teeth 32 grip the aneurysm 14, it is not necessary for the blades to have rough surfaces, and the spring pressure can be limited to that necessary to cause the blades 26 and 28 to close off the neck of the aneurysm 14 firmly without need for excessive pressures which could cause injury to the intimal layer of a cerebral artery or the like, if a clip is inadvertently improperly positioned on an artery. In particular, if an overly strong clip is accidentally placed on the main artery and, in a second attempt, is replaced correctly on the aneurysm, the original placement of the clip with its strong closure pressure can cause injury to the intimal layer of a cerebral artery, and limited spring pressure provides less likelihood of such injury.

The clip illustrated in the drawing and described above is subject to structural modification without departing from the spirit and scope of the appended claims.

Having described our invention, what we claim as new and desire to secure by Letters Patent is:

1. An aneurysm clip which comprises a pair of elongated flat blades having elongated smooth edges for positioning adjacent a blood vessel, means urging the blades into gripping relation with an aneurysm on the blood vessel, and teeth on edges of the blades spaced from the smooth edges thereof for engaging and gripping the aneurysm spaced from the blood vessel, the teeth on each blade extending through spaces between teeth on the other blade into overlapping relationship with the other blade when the clip is closed, gripping faces of the blades being flat and the blades being urged into flatwise relation for gripping the aneurysm.

2. An aneurysm clip as in claim 1 wherein the teeth on each of the blades extend toward the other blade and the teeth intermesh when in gripping relation.

* * * * *

UNITED STATES PATENT AND TRADEMARK OFFICE
CERTIFICATE OF CORRECTION

PATENT NO. : 4,340,061
DATED : July 20, 1982
INVENTOR(S) : George Kees, Jr. and Set Shahbabian It is certified that error appears in the above-identified patent and that said Letters Patent are hereby corrected as shown below:

[73] Assignee: "Mayfield Education and Research Fund, Cincinnati, Ohio" should be -- --
Mayfield Education and Research Fund, Cincinnati, Ohio, part interest --.

Signed and Sealed this

Fourteenth Day of August 1984

[SEAL]

Attest:

GERALD J. MOSSINGHOFF

Attesting Officer

Commissioner of Patents and Trademarks